US005430213A

United States Patent [19]

Hendriksen et al.

[11] Patent Number: 5,430,213

[45] Date of Patent: Jul. 4, 1995

[54] PROCESS FOR PRODUCING 1,4-DIENES

[75] Inventors: Dan E. Hendriksen, Kingwood; Stephanie Linscott, Baytown, both of Tex.

[73] Assignee: Exxon Chemical Patents Inc., Linden, N.J.

[21] Appl. No.: 58,616

[22] Filed: May 6, 1993

[51] Int. Cl.[6] .......... C07C 2/76

[52] U.S. Cl. .......... 585/601

[58] Field of Search .......... 585/601

[56] References Cited

U.S. PATENT DOCUMENTS

| | | | |
|---|---|---|---|
| 3,405,193 | 10/1968 | Hata et al. . | |
| 3,405,194 | 10/1968 | Iwamoto et al. . | |
| 3,407,244 | 10/1968 | Sarafidis . | |
| 3,445,540 | 5/1969 | Sarafidis . | |
| 3,496,247 | 2/1970 | Yuguchi et al. . | |
| 3,524,896 | 8/1970 | Bozik et al. . | |
| 3,548,022 | 12/1970 | Iwamoto et al. . | |
| 3,574,139 | 4/1971 | Harder . | |
| 3,647,901 | 3/1972 | Sarafidis . | |
| 3,647,902 | 3/1972 | Henrici et al. . | |
| 3,669,949 | 6/1972 | Yoo . | |
| 4,201,731 | 5/1980 | Lyons et al. | 585/361 |
| 5,113,033 | 5/1992 | Myers et al. | 585/601 |

FOREIGN PATENT DOCUMENTS

| | | |
|---|---|---|
| 58/10528 | 1/1983 | Japan . |
| 60/89436 | 5/1985 | Japan . |

OTHER PUBLICATIONS

A. Miyake, et al., "A New Process for 1,4-Diene Synthesis" Proceedings, Seventh World Petroleum Congress, vol. 5, pp. 317-323 (1967).

M. Iwamoto, et al., "Reaction of Butadiene With Ethylene. IV. Synthesis of 1,4-Hexadiene By A Cobaltous Chloride-Ditertiary Phosphine Complex And An Organoaluminum Compound Catalyst", Bull. Chem. Soc. Japan, vol. 41, pp. 150-155 (1968).

M. Iwamoto, et al., "Preparation of 3-Methyl-1,4-Heptadiene, 3-Ethyl-1,4-Hexadiene and Methyl-1,4-Hexadienes", J. Organic Chem. 32, 4148-4149 (1967).

Kagawa, T., et al., "Effects of Ditertiary Phosphine Ligands in Co-Dimerizatin of Butadiene and Ethylene Catalyzed by Cobaltous Chloride-Ditertiary Phosphine-Triethylaluminum", Bull. Chem. Soc. Japan, 43, 1250-1251 (1970).

Henrici-Olive, et al., "Codimerization of Butadiene and Ethylene", J. Organometallic Chem., 35, 381-388 (1972).

Chemical Abstracts, vol. 103, No. 15, 14 Oct. 1985, Columbus, Ohio, US; abstract No. 122975n, p. 682.

*Primary Examiner*—Asok Pal
*Assistant Examiner*—E. D. Irzinski
*Attorney, Agent, or Firm*—L. K. Russell

[57] ABSTRACT

Pure 1,4-dienes are produced at high rates of reaction by reacting a conjugated diene and an alpha monoolefin at a temperature below 70° C. in the presence of a catalyst consisting essentially of a 1,3-bis(diphenylphosphino)propane ligand of Co(II)(acetylacetonate)$_2$ or Co(III)(acetylacetonate)$_3$ or $CoCl_2$ in combination with a dialkylaluminum halide such as diethylaluminum chloride.

19 Claims, No Drawings

PROCESS FOR PRODUCING 1,4-DIENES

FIELD OF THE INVENTION

This invention relates to processes for the preparation of 1,4-dienes from the reaction of a conjugated diolefin with an alpha-monoolefin, and more particularly, to such processes involving a catalyst system including a salt of cobalt, a tertiary diphosphine, and an organoaluminum compound.

BACKGROUND OF THE INVENTION 1,4-Dienes are useful as comonomers in polyolefin polymers since they allow the polymer to be cross-linked.

In U.S. Pat. No. 3,405,194 (the '194 patent), Iwamoto et al disclose a method of producing hexadienes by the reaction of an alpha-monoolefin with a conjugated diolefin in the presence of a catalyst system of a salt of cobalt or iron, a tertiary diphosphine, and an organoaluminum compound. Tertiary diphosphines are described in the '194 patent to include 1,2-bis(diphenylphosphino)ethane (herein sometimes abbreviated "dppe") and 1,3-bis(diphenylphosphino)propane (herein sometimes abbreviated "dppp").

In the '194 patent examples and in a number of contemporaneous and subsequent learned scientific publications and patents, the prior art has taught the importance of reacting a conjugated diolefin with an alpha-monoolefin at temperatures of about 80° C. or more when using a cobalt based catalyst system of the types described in the '194 patent.

Of the 88 examples in the '194 patent, 68 examples (1–53 and 74–88) are directed to a catalyst system of a salt of cobalt, a tertiary diphosphine, and an organoaluminum compound, and 64 of these 68 examples employ a temperature of at least 80° C. (example 2 is at 70° C. and examples 39, 47 and 76 are at 50° C., all with a catalyst system including a cobalt complex with dppe).

In "A New Process for 1,4-Diene Synthesis", A. Miyake, G. Hata, M. Iwamoto, and S. Yuguchi, *Proceedings of the Seventh World Petroleum Congress,* 1967, volume 5, 317, the authors described the superiority of a cobalt diphosphine system of $CoCl_2$-dppe in combination with an aluminum trialkyl, specifically, triethylaluminum, at 80° C., in producing 1,4-hexadiene at a rate 100 fold higher than an iron based system of Fe(III)-(acetylacetonate)$_3$-$Et_3Al$ at 30° C. and 10 fold greater than a $FeCl_3$-dppe-$Et_3Al$ system at 80° C. (each also described in the '194 patent).

The effects of reaction temperature on reaction rate for butadiene conversion are particularly described for the catalyst system of $CoCl_2$-dppe-$Et_3Al$ in "Reaction of Butadiene with Ethylene. IV. Synthesis of 1,4-Hexadiene by a Cobalt Chloride-Ditertiary Phosphine Complex and an Organoaluminum Compound Catalyst", M. Iwamoto and S. Yuguchi, *Bulletin of the Chemical Society of Japan,* 1968, 41, 150. Apparent optimum reaction temperatures are said to be in the range of 80° to 100° C. Two examples achieved 97% selectivity at 80° C. Below 80° C., rate of conversion is shown to fall precipitously, and at temperatures higher than 100° C. a considerable loss of selectivity from isomerization of 1,4-hexadiene to conjugated dienes, mainly to 2,4-hexadiene, is reported.

Henrici-Olivé et al, in "Codimerization of Butadiene and Ethylene," *Journal of Organometallic Chemistry,* vol. 35, p. 381 (1972), a study of the catalytic system described in the above cited articles by Iwamoto et al, report that temperature of reaction appears "critical" for high selectivity using $CoCl_2$-dppe-$Et_3Al$ in dichloroethane. The authors state that: "between 80° and 110° cis-1,4-hexadiene is formed in high yield, whereas below 80° more ethylene than butadiene is consumed, with the result that $C_8$ compounds are produced. Above 110° 1,4-hexadiene is isomerized to 2,4-hexadiene." (p. 381). Teaching the same is U.S. Pat. No. 3,647,902, to Henrici-Olivé et al (where the catalyst system is $CoCl_2$-dppe-$Et_3Al$ in a halogenated hydrocarbon solvent), stating the temperature must be not less than 80° C. when ethylene is reacted with 1,3-butadiene, or poor selectivity results (col. 2, lines 13–24).

The foregoing teachings in the prior art on conducting the reaction at temperatures of at least 80° C. encompass specific described cobalt catalyst systems where the diphosphine ligand is dppp. In the '194 Patent, examples 18–27, 43 and 88 employ dppp as a cobalt catalyst ligand. In examples 18–27, the cobalt complex is $CoCl_2$ and dppp; in examples 43 and 48, the cobalt complex is the acetyl acetonate of trivalent cobalt, i.e., $Co(C_5H_7O_2)_3$, with the dppp ligand. (Herein, for brevity and clarity, acetylacetonate is sometimes referred to by the abbreviation "acac"; for example, the acetylacetonate of trivalent cobalt is $Co(acac)_3$). The dppp ligand thus is $Co(acac)_3$-dppp. The organoaluminum compound used in examples 18–27, 43 and 88 is trimethylaluminum ("TMAL") or triethylaluminum ("TEAL") when the cobalt salt is $CoCl_2$ and is sometimes diethylaluminum chloride ("DEAC") when the cobalt salt is $Co(acac)_3$. In all these '194 patent examples employing the dppp ligand, the temperatures are in the range 80°-102° C.

"Effects of Ditertiary Phosphine Ligands in Co-dimerization of Butadiene and Ethylene Catalyzed by Cobalt Chloride-Ditertiary Phosphine-Triethylaluminum" T. Kagawa, Y. Inoue, and H. Hashimoto, *Bulletin of the Chemical Society of Japan,* 1970, 43, 1250, reports results for testing a $CoCl_2$-$Ph_2P(CH_2)_nPPh_2$-$Et_3Al$ catalyst system (Ph=phenyl, n=1, 2, 3, 4 etc.) for effect of length of the methylene chain between the two phosphorous atoms on cis-1,4-hexadiene formation at 80°-90° C. The data presented for the system $CoCl_2$-dppp-$Et_3Al$ indicate a relatively low yield to 1,4-hexadiene on butadiene.

The temperature teachings in the art have applied whether the conjugated diolefin is butadiene or isoprene. The '194 patent in examples 74–75, 77–82 employs $CoCl_2$-dppe-$Et_3Al$ at 80° or 100° C. to react isoprene with ethylene. In "Preparation of 3-Methyl-1,4-heptadiene, 3-Ethyl-1,4-hexadiene, and Methyl-1,4-hexadienes" by M. Iwamoto, K. Tani, H. Igaki, and S. Yuguchi, *Journal of Organic Chemistry* 1967, 32, 4148, reaction of isoprene with ethylene is reported rapid and selective (97.2–99%) at 80°–98° C. with the $CoCl_2$-dppe-$Et_3Al$ catalyst system.

Even variants of the cobalt catalyst systems teach reaction conversion of conjugated diolefins to 1,4-dienes at a 80° C. minimum. U.S. Pat. No. 3,445,540 uses a triphosphine instead of a diphosphine, and U.S. Pat. No. 3,574,139 uses cobalt complexed with two diphosphines, i.e., bis [ethylene bis(diphenylphosphine)] cobalt (0) or bis[ethylene bis(diphenylphosphine)] cobalt (I) hydride. Both of these two patents state that "temperatures below 80° C. may be too slow for operating convenience. The preferred temperature range lies between 80° and 120° C. . . ." (3,574,139, col. 3, lines 70–74; 3,445,540, col. 5, lines 35–39).

In the '194 patent, toluene is the solvent in examples 18–23 and 43; halogenated hydrocarbon solvents are used in examples 24–27 and 88. Halogenated hydrocarbon solvents are instructed to be used to improve selectivity when the intended hexadiene is 1,4-hexadiene, and to provide the further advantage of easier cobalt catalyst handling, since these solvents dissolve the cobalt complex completely (col. 4, lines 60–67). In the article by Henrici-Olivé et al cited above, halogenated hydrocarbon solvents are said favored, because $CoCl_2$-dppe is insoluble in toluene and alkylation reactions of transition metal salts with aluminum alkyls are faster and more complete in halogenated solvents than in aromatics. To the same point is U.S. Pat. No. 3,647,902.

The highest selectivity, essentially 100 percent selectivity, is desired, in order to maximize production of pure 1,4-dienes, thereby eliminating the difficult separation of 2,4-diene and other by-products to satisfy the commercial need for pure 1,4-dienes. An object of this invention is the preparation of 1,4-dienes with essentially 100% selectivity from reaction of conjugated diolefins with an alpha-olefin.

An object of this invention is provision of a process providing essentially pure 1,4-dienes from conjugated diolefins at high rates of reaction.

An object of this invention is provision of a process providing essentially pure 1,4-dienes from conjugated diolefins at high rates of reaction and high catalyst productivity.

In order to obtain highest reaction rates per unit of catalyst, the prior art has employed halogenated hydrocarbon solvents for preformed catalysts, particularly the favored $CoCl_2$-dppe/TEAL catalyst system of the above referenced prior art. However, halogenated solvents are environmentally disfavored, are corrosive to equipment, and consequently are commercially unattractive as a means of improving catalytic reaction rates and product yields. An object of this invention is provision of a process promoting reaction of conjugated diolefins and alpha-olefins at high rates of reaction without the use of halogenated hydrocarbon solvents.

We have found that production of essentially pure 1,4-dienes from conjugated diolefins and an alpha-olefin (essentially 100% selectivity) can be realized, using a particular combination of certain cobalt compounds, a particular diphosphine and a dialkylaluminum halide. Surprisingly, contrary to the teachings of the prior art, we have found that this result is achieved at temperatures less than 80° C. Further, we have found this exceptional selectivity at these reaction temperatures in this particular catalyst system is accompanied by vastly increased rates of reaction and catalyst productivity, indicative of a very reactive species of catalyst. Still more surprisingly, we have found these results can be accomplished without use of the corrosive and environmentally disfavored halogenated hydrocarbon solvents that the prior art teaches should be used to improve yields.

SUMMARY OF THE INVENTION

Our invention is a process for preparing pure 1,4-dienes, which comprises reacting a conjugated diolefin with an alpha-olefin in the presence of a catalyst system which consists essentially of (1) $Co(acac)_n$-dppp, or a preformed complex of $CoCl_2$(dppp), where "acac" is acetylacetonate, "n" equals the valence of cobalt, and "dppp" is 1,3-bis(diphenylphosphino) propane, and (2) a dialkylaluminum chloride, present at a molar ratio of Al/Co of at least 5:1, in a hydrocarbon solvent reaction medium, at reaction conditions controlled in a temperature range less than 70° C. and at an alpha-olefin partial pressure range of from about 0.5 to about 100 atmospheres effective to convert the conjugated diolefin to a 1,4-diene with essentially 100% selectivity. By "pure" is meant more than about 99% 1,4-diene, preferably approaching or equaling 100% 1,4-diene.

DESCRIPTION OF THE PREFERRED EMBODIMENTS

The catalysts employed in the process of this invention are $Co(acac)_n$-dppp (n equals the valence of cobalt) and preformed $CoCl_2$-dppp, and the cocatalysts are selected from dialkylaluminum halides of the general formula R'R"AlX, where R is an alkyl, suitably in the $C_1$–$C_4$ range, Al is aluminum, and X signifies a halide, for example, dimethylaluminum chloride, diethylaluminum chloride, di-n-propylaluminum halides, di-isopropylaluminum halides, and di-isobutylaluminum halides. Conjugated diolefins employed suitably are 1,3-butadiene (sometimes referred to herein simply as butadiene or "BD") or isoprene, and the alpha monoolefins suitably are ethylene or propylene. Where the reactants are butadiene and ethylene, pure 1,4-hexadiene is produced.

When the cobalt catalyst is $Co(acac)_n$, preferably from about 0.9 to less than 2 mols of dppp are combined with the $Co(acac)_n$ in the reaction medium. Advantageously, the mol ratio of dppp to $Co(acac)_n$ is effective to produce a rate of reaction, at the reaction temperature less than 70° C., of at least about 120 mols of 1,4-hexadiene per mol of cobalt per minute, where the conjugated diene is butadiene or where isoprene or propylene are the reactants, of at least 30 mols of pure product per mol of cobalt per minute. Advantageously, the mol ratio of dppp to $Co(acac)_n$ is effective for a catalyst productivity, at the reaction temperature less than 70° C., of at least about 1000 mols of 1,4-hexadiene per mol of cobalt.

In a preferred embodiment, the catalyst is $Co(acac)_2$-dppp and diethylaluminum chloride or $Co(acac)_3$-dppp and diethylaluminum chloride.

In another preferred embodiment, the process catalyst system is $CoCl_2$-dppp and diethylaluminum chloride. Using this system in the process, the rate of the reaction suitably exceeds 100 mols of 1,4-hexadiene produced per mol of cobalt per minute. The most preferred embodiment is a process for preparing pure 1,4-hexadiene, which comprises reacting butadiene with ethylene in the presence of a catalyst system consisting of (a) Co(II)(acetylacetonate)$_2$ and 1,3-bis(diphenylphosphino)propane in a mol ratio of about 1:1.5, and (b) diethylaluminum chloride, at a mol ratio of Al/Co of at least 5:1, in a hydrocarbon solvent at reaction conditions controlled in a temperature range from about 50° C. to 69° C. and an alpha-olefin partial pressure range from about 0.5 to about 100 atmospheres, effective to convert the butadiene to 1,4-hexadiene with essentially 100% selectivity at a reaction rate of at least 500 mols of 1,4-hexadiene produced per mol of cobalt per minute.

Optionally, the catalyst system employing the $CoCl_2$-dppp preformed complex further includes triethylaluminum with no more than two molar equivalents of triethylaluminum per mol of the preformed complex.

The improved catalyst preferably uses diethylaluminum chloride as the dialkylaluminun halide cocatalyst. This is used alone when the catalyst is formed in situ form $Co(acac)_3$ or $Co(acac)_2$. When the improved preformed complex $CoCl_2$-dppp is used, up to two equivalents of triethylaluminum ($Et_3Al$:Co not more than 2) may be added with the diethylaluminum chloride.

The temperature of the reaction has a dramatic effect on the selectivity of the reaction to the desired 1,4-diene with the catalyst systems of the present invention. The process temperature is less than 70° C., suitably from about 50° C. and less than 70° C., and preferably, about 60° C. In the Examples 1 through 3 and 5 through 10 below of the present improved process, the temperature of reaction is 60° C. Selectivity to 1,4-hexadiene in these Examples approaches 100%. The reaction rate and catalyst productivity are very high with the improved catalyst despite the improvement in selectivity by use of a lower temperature.

The improved process may use a hydrocarbon solvent such as toluene or xylene or the 1,4-diene product of the reaction, e.g. 1,4-hexadiene from the reaction of butadiene with ethylene. No separation of a solvent from the product is needed when the product is used as the solvent for the reaction. Halogenated solvents are usable but unnecessary for adequate results.

The present invention is illustrated by the following Examples 1 through 3 and 5 through 10. In all these examples except Example 5, data is given on (1) conversion of the charged conjugated diene by a catalyst system, i.e., the percent conversion of a conjugated diene charge to all products of reaction, (2) productivity of a catalyst system, i.e., yield of the desired 1,4-diene product per mol of cobalt catalyst, (3) selectivity of the catalyst system for the desired 1,4-diene, i.e., the percent of all the products which is the desired 1,4-diene, (4) the observed first order rate constant of the catalyst system, and (5) the overall reaction rate of the catalyst system.

Thus, "conversion" of diene (expressed as a percentage) is mols of diene converted to all products divided by mols of diene charged (for 1,3-butadiene, per cent conversion is the per cent of mol 1,3-butadiene converted to all products/mol 1,3-butadiene charged). "Selectivity" (expressed as a percentage) is the mols yield of a particular diene product divided by the mols of diene converted to all products. Thus, selectivity of the catalyst system for 1,4-hexadiene with a charge of ethylene and 1,3-butadiene is mols of 1,4-hexadiene yield-/mols 1,3-butadiene converted to all products. "Yield" of a desired product results from multiplying the selectivity percentage of the catalyst system for that desired product under the conditions of the reaction times the aggregate mols of all the products into which the charge diene is converted.

The first order rate constant in the Examples is helpful for within system comparisons. As is shown, the first order reaction rate constant per mmole of cobalt can be about 15. Ethylene pressure in a 500 mL vessel was recorded vs. time during the reaction as the ethylene was fed to the reactor to keep the pressure constant. The reaction was permitted to proceed for a long enough time to determine the pressure of ethylene remaining after all butadiene had been consumed. The $P_{time}-P_{final}$ is then proportional to the amount of butadiene remaining in the autoclave. The reaction is first order for butadiene, and a plot of $\ln(P_{time}-P_{final})$ vs. time yields a straight line, the slope of which is the observed rate constant.

Example 1

In a nitrogen-filled glove box, 6 mg (0.01 mmole) of a preformed complex of $CoCl_2$(1,3-bis(diphenylphosphino)propane) was dissolved in 80 mL anhydrous toluene. To this was added with stirring a 25 wt % solution of diethylaluminum chloride in toluene (0.6 mL, 1.0 mmole). This solution was transferred under nitrogen to a 300 mL stirred autoclave and heated to 60° C. With the stirrer stopped, butadiene (20.8 g, dried and with t-butylcatechol inhibitor removed by passing through a column of 3A molecular sieve and a column of basic alumnia) was pressured into the autoclave using ethylene and the total pressure brought to 2089 kPa with the ethylene. The stirrer was started, and the total pressure in the autoclave was kept constant at 1400 kPa (200 psig) by feeding ethylene through a pressure regulator from a 500 mL vessel containing ethylene at a higher pressure. The rate of the reaction was monitored by the drop in pressure in this vessel. After the consumption of ethylene had essentially stopped (71 minutes) the autoclave was cooled rapidly in an ice bath. The autoclave was vented, opened, and the contents removed and analyzed by gas chromatography. Conversion of butadiene was 97%. Selectivity to cis-1,4-hexadiene was 99.9%. The only other product of the reaction was 2,4-hexadiene. Vinylcyclohexene, which is an impurity in the butadiene, was also found. The observed first-order rate constant for the reaction was 0.106 $min^{-1}$. The rate constant per mmole Co is 10.6.

Example 2

This example illustrates that the rate of the reaction doubles when the amount of starting cobalt complex is doubled. The reaction was carried out in a similar manner as in Example 1.

11 mg (0.02 mmole) of the preformed complex of $CoCl_2$(1,3-bis(diphenylphosphino)propane) was dissolved in 80 mL anhydrous toluene. To this was added with stirring a 25 wt % solution of diethylaluminum chloride in toluene (0.6 mL, 1.0 mmole). Only 11.8 g of butadiene was added to the autoclave, and consumption of ethylene stopped after 37 minutes. Conversion of butadiene was 94%. Selectivity to cis-1,4-hexadiene was 100%. A trace of 2,4-hexadiene (less than 0.1%) was found. The observed first-order rate constant for the reaction was 0.206 $min^{-1}$. The rate constant per mmole Co id 10.3.

Example 3

This example illustrates the use of two equivalents of triethylaluminum per cobalt in addition to an excess of diethylaluminum chloride.

The reaction was carried out in a similar manner as Example 1. The preformed complex $CoCl_2$(1,3-bis(diphenylphosphino)propane) (11 mg, 0.02 mmole) was dissolved in 80 mL anhydrous toluene. To this was added with stirring a 25 wt % solution of diethylaluminum chloride in toluene (0.5 mL, 0.96 mmole) and also a 2.5 wt % solution of triethylaluminum in toluene (0.2 mL, 0.04 mmole). Butadiene (22.7 g) was added to the autoclave, and consumption of ethylene stopped after 25 minutes. Conversion of butadiene was 98%. Selectivity to cis-1,4-hexadiene was 100%. A trace of 2,4-hexadiene (less than 0.1%) was found. The observed first-order rate constant for the reaction was 0.206 $min^{-1}$. The rate constant per mmole Co is 10.3.

Tables 1,2 and 3. The data of Examples 1, 2 and 3 for cis-1,4-hexadiene production using a preformed cobalt chloride-dppp catalyst and DEAC cocatalyst at a temperature less than 70° C. are set forth in Table 1, arranged in descending order of overall rate of reaction. The surprising difference between these results and those using the same catalyst but with a TEAL cocatalyst at temperatures above 70° C. are seen by comparison of the data of Table 1 with the data of following Table 2, a tabulation of data from examples contained in U.S. Pat. No. 3,405,194, also arranged in the same descending order. There is an order of magnitude greater rate of reaction when using a preformed cobalt chloride-dppp catalyst and DEAC cocatalyst at less than 70° C. in accordance with our invention, compared to using a preformed cobalt chloride-dppp catalyst and TEAL cocatalyst at more than 70° C.; further, the selectivity to 1,4-hexadiene is essentially 100% when using the preformed cobalt chloride-dppp catalyst and DEAC cocatalyst at less than 70° C., but is less than 90% with the older catalyst system at the higher temperatures. The same improvement exists whether the prior art process $CoCl_2$-dppp is preformed or not. Table 3 tabulates data calculated from examples in the '194 patent in which the $CoCl_2$-dppp catalyst was formed in situ and used in the presence of TEAL at temperatures above 70° C. Reaction rates are on the same order as the preformed catalyst set out in Table 2. In Tables 1, 2 and 3, "Al" is aluminum, "Co" is cobalt, "BD" is butadiene, "1,4-HD" is 1,4-hexadiene, "Prodt'y" is catalyst productivity, "Conv" is conversion of butadiene to 1,4-hexadiene, and "Select'y" is selectivity of conversion of butadiene to 1,4-hexadiene.

TABLE 1

Preformed $CoCl_2$-dppp Catalyst, DEAC Cocatalyst, Less Than 70° C.

| Ex. | Co Compd | Co (mmol) | Organo-Aluminum Cmpd | Al (mmol) | Al/Co | Solvent | BD (gms) | BD (mmol) | Di/Co | Time (min) | Temp (C.) |
|---|---|---|---|---|---|---|---|---|---|---|---|
| 3 | CoCl2(dppp) | 0.02 | DEAC + TEAL | 1.00 | 50 | toluene | 22.70 | 420 | 21,019 | 25 | 60 |
| 1 | CoCl2(dppp) | 0.01 | DEAC | 1.00 | 100 | toluene | 20.80 | 385 | 38,519 | 71 | 60 |
| 2 | CoCl2(dppp) | 0.02 | DEAC | 1.00 | 50 | toluene | 11.80 | 219 | 10,926 | 37 | 60 |

| Ex. | 1,4-HD Yield (g) | 1,4-HD Yield (mols) | Prodt'y (mol/mol) | Rate (mol/mol/min) | Observed 1st Order Rate K (min-1) | Rate per mmol Co | Conv (%) | Select'y (%) |
|---|---|---|---|---|---|---|---|---|
| 3 | 33.78 | 0.41 | 20,563 | 823 | 0.206 | 10.30 | 98 | 100 |
| 1 | 30.61 | 0.37 | 37,262 | 525 | 0.106 | 10.60 | 97 | 99.9 |
| 2 | 16.84 | 0.21 | 10,253 | 277 | 0.206 | 10.30 | 94 | 100 |

TABLE 2

U.S. Pat. No. 3,405,194: Preformed $CoCl_2$-dppp Catalyst, TEAL Cocatalyst, More than 70° C.

| Ex. | Co Cmpd | Co (mmol) | Organo-Aluminum Cmpd | Al (mmol) | Al/Co | Solvent | BD (gms) | BD (mmol) | Di/Co |
|---|---|---|---|---|---|---|---|---|---|
| 23 | CoCl2(dppp) | 0.25 | TMAL | 15.65 | 63 | toluene | 114 | 2,111 | 8,444 |
| 24 | CoCl2(dppp) | 0.18 | TEAL | 8.47 | 46 | ethyleneCl | 85.7 | 1,587 | 8,625 |
| 21 | CoCl2(dppp) | 0.25 | TEAL | 10.95 | 44 | toluene | 100 | 1,852 | 7,407 |
| 22 | CoCl2(dppp) | 0.13 | TEAL | 10.95 | 88 | toluene | 100 | 1,852 | 14,815 |
| 20 | CoCl2(dppp) | 0.50 | TEAL | 1.46 | 3 | toluene | 100 | 1,852 | 3,704 |
| 19 | CoCl2(dppp) | 0.50 | TEAL | 5.11 | 10 | toluene | 20.5 | 380 | 759 |
| 18 | CoCl2(dppp) | 0.50 | TEAL | 5.11 | 10 | toluene | 20.5 | 380 | 759 |

| Ex. | Time (min) | Temp (C.) | 1,4-HD Yield (g) | 1,4-HD Yield (mols) | Prodt'y (mol/mol) | Rate (mol/mol/min) | Conv (%) | Select'y (%) |
|---|---|---|---|---|---|---|---|---|
| 23 | 180 | 80–90 | 161.80 | 1.97 | 7,879 | 43.77 | 107.41 | 87.01 |
| 24 | 120 | 98–102 | 67.20 | 0.82 | 4,446 | 37.05 | 65.05 | 79.37 |
| 21 | 180 | 80–90 | 116.70 | 1.42 | 5,683 | 31.57 | 89.25 | 86.11 |
| 22 | 180 | 80–90 | 51.80 | 0.63 | 5,045 | 28.03 | 40.41 | 84.41 |
| 20 | 156 | 80–90 | 105.80 | 1.29 | 2,576 | 16.51 | 93.87 | 74.22 |
| 19 | 60 | 80–90 | 24.40 | 0.30 | 594 | 9.90 | 112.59 | 69.61 |
| 18 | 1140 | 80–90 | 13.40 | 0.16 | 326 | 0.29 | 149.37 | 28.82 |

TABLE 3

U.S. Pat. No. 3,405,194: In Situ $CoCl_2$-dppp Catalyst, TEAL Cocatalyst, More than 70° C.

| Ex. | Co Cmpd | Co (mmol) | Organo Aluminum Cmpd | Al (mmol) | Al/Co | Solvent | BD (gms) | BD (mmol) |
|---|---|---|---|---|---|---|---|---|
| 27 | CoCl2 + dppp | 0.13 | TEAL | 7.27 | 58 | ethyleneCl | 67 | 1,241 |
| 26 | CoCl2 + 0.5 dppp | 0.25 | TEAL | 7.30 | 29 | ClBz | 67 | 1,241 |
| 25 | CoCl2 + dppp | 0.50 | TEAL | 7.30 | 15 | ClBz | 67 | 1,241 |

| Ex. | Di/Co | Time (min) | Temp (C.) | 1,4-HD Yield (g) | 1,4-HD Yield (mols) | Prodt'y (mol/mol) | Rate (mol/mol/min) | Conv (%) | Select'y (%) |
|---|---|---|---|---|---|---|---|---|---|
| 27 | 9,926 | 180 | 80–90 | 83.70 | 1.02 | 8,151 | 45.28 | 85.75 | 95.93 |
| 26 | 4,963 | 180 | 80–90 | 78.50 | 0.96 | 3,822 | 21.23 | 92.72 | 83.21 |

TABLE 3-continued

| U.S. Pat. No. 3,405,194: In Situ $CoCl_2$-dppp Catalyst, TEAL Cocatalyst, More than 70° C. | | | | | | | | | |
|---|---|---|---|---|---|---|---|---|---|
| 25 | 2,481 | 120 | 80 | 85.00 | 1.04 | 2,069 | 17.24 | 96.80 | 86.30 |

Comparative Example 4 and Example 5 which follow demonstrate that use of excess triethylaluminum (TEAL) as cocatalyst at less than 70° C. yields unsatisfactory results with the preformed cobalt chloride-dppp catalyst system of the present invention compared to the use of excess diethylaluminum chloride (DEAC) as cocatalyst. In these two examples the preformed complex $CoCl_2$-dppp is initially dissolved in a small amount of chlorobenzene in order to assure it is completely dissolved before addition of the cocatalyst.

Comparative Example 4

The reaction was carried out in a similar manner as in Example 1. The preformed complex $CoCl_2$-dppp (27 mg, 0.05 mmole) was dissolved in 10 mL anhydrous chlorobenzene. To this was added with stirring a 25 wt % solution of triethylaluminum (TEAL) in toluene (0.8 mL, 1.5 mmole). Anhydrous toluene (70 mL) was then added to this solution. Butadiene (21.6 g) was added to the autoclave at 60° C., and the reaction was allowed to proceed for 14 minutes. No significant uptake of ethylene was observed during this time. Conversion of butadiene to cis-1,4-hexadiene was less than 1%. No other product of the reaction was observed.

Example 5

The reaction was carried out in a similar manner as in Example 1. The preformed complex $CoCl_2$-dppp (27 mg, 0.05 mmole) was dissolved in 10 mL anhydrous chlorobenzene. To this was added with stirring a 25 wt % solution of diethylaluminum chloride (DEAC) in toluene (0.8 mL, 1.5 mmole). Anhydrous toluene (70 mL) was then added to this solution. Butadiene (21.1 g) was added to the autoclave at 60° C., and the reaction was allowed to proceed for 30 minutes. During the first few minutes the reaction rate was so fast that the temperature could not be controlled. Consumption of ethylene had essentially ceased after 6 minutes. Conversion of butadiene was greater than 99%. Selectivity to cis-1,4-hexadiene was 99.9%; the only other product of the reaction was 2,4-hexadiene.

Example 6

This Example illustrates the use of $Co(acac)_3$ as the starting cobalt compound. Twice as much of this cobalt compound is needed to achieve essentially the same observed first-order rate constant as with the preformed complex.

The reaction was carried out in a similar manner as Example 1. Cobalt(III) acetylacetonate (14 mg, 0.04 mmole), and 1,3-bis(diphenylphosphino)propane (19 mg, 0.045 mmole) were dissolved in 80 mL anhydrous toluene. To this was added with stirring a 25 wt % solution of diethylaluminum chloride in toluene (0.6 mL, 1.0 mmole). Butadiene (24.0 g) was added to the autoclave, and consumption of ethylene stopped after 27 minutes. Conversion of butadiene was 99%. Selectivity to cis-1,4-hexadiene was 99.9%. The only other product of the reaction was 2,4-hexadiene. The observed first-order rate constant for the reaction was 0.195 $min^{-1}$. The rate constant per mmole Co is 4.9.

Example 7

This Example illustrates the use of $Co(acac)_2$ as the starting cobalt compound. Use of this cobalt compound in the same relative molar amounts results in a rate of reaction about one and a half times that found when the preformed complex $CoCl_2$-dppp is used (as in Example 1).

The reaction was carried out in a similar manner as in Example 1. Cobalt(II) acetylacetonate (2.6 mg, 0.01 mmole) and dppp (6.2 mg, 0.015 mmole, dppp=1,3-bis(-diphenylphosphino)propane) were dissolved in 80 mL anhydrous toluene. This was accomplished by using 2 mL of a stock solution made by dissolving $Co(acac)_2$ (26 mg, 0.10 mmole) and dppp (62 mg, 0.15 mmole) in 20 mL of anhydrous toluene. To the 80 mL catalyst was added with stirring a 25 wt % solution of DEAC in toluene (0.6 mL, 1.0 mmole). Butadiene (22.5 g) was added to the autoclave at 60° C., and consumption of ethylene stopped after 32 minutes. Conversion of butadiene was 98%. Selectivity to cis-1,4-hexadiene was 100%; a trace of 2,4-hexadiene (less than 0.1%) was found. The observed first-order rate constant for the reaction was 0.150 $min^{-1}$. The rate constant per mmole Co is 15.00.

Example 8

This Example illustrates the use of the product cis-1,4-hexadiene as solvent for the reaction.

The reaction was carried out in a similar manner as in Example 1. Cobalt(II) acetylacetonate (10 mg, 0.04 mmole) and dppp (19 mg, 0.045 mmole) were dissolved in 80 mL cis-1,4-hexadiene (dried by passing through a column of 3A molecular sieve and alumina under nitrogen). To this was added with stirring a 25 wt % solution of DEAC in toluene (0.6 mL, 1.0 mmole). Butadiene (22.9 g) was added to the autoclave at 60° C., and consumption of ethylene stopped after 23 minutes. Conversion of butadiene was 99%. Selectivity to cis-1,4-hexadiene (based on product formed in the reaction) was 99.9%; the only other product of the reaction was 2,4-hexadiene. The observed first-order rate constant for the reaction was 0.095 $min^{-1}$. The rate constant per mmole Co is 2.38.

Example 9

This Example illustrates the use of isoprene as the conjugated diene reactant. In the reaction of isoprene with ethylene, the product is a mixture of 4-methyl-1,4-hexadiene and 5-methyl-1,4-hexadiene.

The reaction was carried out in a similar manner as in Example 1. Cobalt(II) acetylacetonate (31 mg, 0.12 mmole) and dppp (52 mg, 0.125 mmole) were dissolved in 80 mL anhydrous ortho-xylene. To this was added with stirring a 25 wt % solution of DEAC in toluene (3.3 mL, 6 mmole). Isoprene (23.6 g, dried by passing through a column of 3A molecular sieve and alumina) was added to the autoclave at 60° C., and consumption of ethylene stopped after 33 minutes. Conversion of isoprene was 99%. Selectivity to 4-methyl-1,4-hexadiene (88%) and 5-methyl-1,4-hexadiene (12%) was essentially 100%. The observed first-order rate constant for the reaction was 0.218 $min^{-1}$. The rate constant per mmole Co is 1.82.

Comparative Example 10

This comparative Example shows the importance of using a molar ratio of dppp ligand to $Co(acac)_n$ that is less than two. In this example, even through the amount of the cobalt salt of highest activity was quadrupled and a 2:1 ratio of dppp ligand to $Co(acac)_2$ was used, a much slower rate of reaction resulted. A molar ratio of dppp ligand of from a little less than unity to less than 2 is satisfactory, as in Example 7, which uses a dppp:Co ratio of 1.5:1, yet achieves significantly greater activity with one-fourth the amount of cobalt.

TABLE 4

Co(acac)ₙ-dppp Catalyst, DEAC Cocatalyst, Less Than 70° C.

| Ex. | Co Cmpd | Co (mmol) | Organo Aluminum Cmpd | Al (mmol) | Al/Co | Solvent | Di | Diole (gms) | Diole (mmol) | Di/Co | C= |
|---|---|---|---|---|---|---|---|---|---|---|---|
| 7 | Co(acac)2 + 1.5 dppp | 0.01 | DEAC | 1.00 | 100 | toluene | BD | 22.5 | 417 | 41,667 | C2 |
| 8 | Co(acac)2 + dppp | 0.04 | DEAC | 1.00 | 25 | 1,4-HD | BD | 22.9 | 424 | 10,602 | C2 |
| 6 | Co(acac)3 + dppp | 0.04 | DEAC | 1.00 | 25 | toluene | BD | 24.00 | 444 | 11,111 | C2 |
| 10 | Co(acac)2 + 2 dppp | 0.04 | DEAC | 1.00 | 25 | toluene | BD | 20.3 | 376 | 9,398 | C2 |
| 9 | Co(acac)2 + dppp | 0.12 | DEAC | 6.00 | 50 | o-xylene | IP | 23.6 | 350 | 2917 | C2 |

| Ex. | Time (min) | Temp (C.) | 1,4-HD Yield (g) | 1,4-HD Yield (mols) | Prodt'y (mol/mol) | Rate (mol/mol/min) | Observed 1st Order Rate K (min-1) | Rate/mmol | Conv (%) | Select'y (%) |
|---|---|---|---|---|---|---|---|---|---|---|
| 7 | 32 | 60 | 33.48 | 0.41 | 40,764 | 1,274 | 0.15 | 15.00 | 98 | 100 |
| 8 | 23 | 60 | 34.39 | 0.42 | 10,468 | 455 | 0.095 | 2.38 | 99 | 99.9 |
| 6 | 27 | 60 | 36.04 | 0.44 | 10,970 | 406 | 0.195 | 4.90 | 99 | 99.9 |
| 10 | 60 | 60 | 23.40 | 0.29 | 7,123 | 119 | 0.04 | 1.00 | 76 | 99.9 |
| 9 | 33 | 60 | 32.99 | 0.34 | 2,858 | 87 | 0.218 | 1.82 | 99 | 100 |

TABLE 5

U.S. Pat. No. 3,405,194: Co(acac)3 - dppp Catalyst, Organoaluminum Cocatalyst, More Than 70° C.

| Ex. | Co Cmpd | Co (mmol) | Organo Aluminum Cmpd | Al (mmol) | Al/Co | Solvent | Di | BD (gms) | BD (mmol) |
|---|---|---|---|---|---|---|---|---|---|
| 43 | Co(acac)3 + dppp | 0.50 | DEAC | 8.0 | 16 | toluene | BD | 16.2 | 0.31 |
| 88 | Co(acac)3 + 2 dppp | 0.10 | TEAL | 7.3 | 73 | ethyleneCl | BD | 21.1 | 0.39 |

| Ex. | Di/Co | C= | Time (min) | Temp (C.) | 1,4-HD Yield (g) | 1,4-HD Yield (mols) | Prodt'y (mol/mol) | Rate (mol/mol/min) | Conv (%) | Select'y (%) |
|---|---|---|---|---|---|---|---|---|---|---|
| 43 | 620 | C2 | 25 | 80 | 23.70 | 0.29 | 577 | 23.08 | 97.96 | 98.34 |
| 88 | 3900 | C3 | 300 | 90–100 | 22.10 | 0.23 | 2298 | 7.66 | 79.33 | 74.26 |

The reaction was carried out in a similar manner as in Example 7 but with a 2:1 dppp:Co mol ratio. Cobalt(II) acetylacetonate (10 mg, 0.04 mmole) and dppp (33 mg, 0.08 mmole) were dissolved in 80 mL anhydrous toluene. To this was added with stirring a 25 wt % solution of DEAC in toluene (0.6 mL, 1.0 mmole). Butadiene (20.3 g) was added to the autoclave at 60° C., and the reaction was allowed to proceed for 60 minutes. At this time conversion of butadiene was only 76%. Selectivity to cis-1,4-hexadiene was 99.9%; the only other product of the reaction was 2,4-hexadiene. The observed first-order rate constant for the reaction was 0.040 $min^{-1}$. The rate constant per mmole Co is 1.00.

Tables 4 and 5. Table 4 sets forth the data of Examples 6–10, in descending order of rate of reaction. The rate of reaction for butadiene to 1,4-hexadiene is at least about 120 (119) mols of 1,4-hexadiene per mol of cobalt catalyst per minute. When less than 2 mols of dppp are used per mol of $Co(acac)_2$ or $Co(acac)_3$, rates of reaction are from about 4 (Examples 6, 8) to about 11 (Example 7) times higher than with 2 mols of dppp per mol of $Co(acac)_2$ or $Co(acac)_3$. In all instances selectivity to 1,4-hexadiene is essentially 100%.

Table 5 tabulates data from the comparable examples of the '194 Patent (these use a $Co(acac)_3$-dppp catalyst). In the '194 patent Example 43, a DEAC cocatalyst is used at a temperature above 70° C. Rate of reaction was very slow, about one fifth that of the minimum preferred rate for the $Co(acac)_n$-dppp system at less than 70° C. In '194 patent Example 88, the monoolefin is propylene and the rate is about a third that of Example 43 of the patent.

In the tables, "IP" is isoprene, "C2" is ethylene, "C3" is propylene, and other abbreviations are the same as in Tables 1, 2 and 3.

In the following comparative Examples 11 through 14, results of using a catalyst system having a dppe catalyst ligand at a temperature less than 70° C. are shown.

Comparative Examples 11 and 12 show that a substantially slower rate of reaction results when 1,2-bis(diphenylphosphino)ethane is combined with $Co(acac)_2$ and DEAC at a temperature of 60° C. This is the case with a molar ratio of dppe:Co of either 1:1 or 2:1.

Comparative Example 11

The reaction was carried out in a similar manner as in Example 1. Cobalt(II) acetylacetonate (10 mg, 0.04 mmole) and dppe (16 mg, 0.04 mmole) were dissolved in 80 mL anhydrous toluene. To this was added with stirring a 25 wt % solution of diethylaluminum chloride in toluene (0.6 mL, 1.0 mmole). Butadiene (22.3 g) was added to the autoclave at 60° C., and the reaction was allowed to proceed for 60 minutes. Conversion of butadiene was 99%. Selectivity to cis-1,4-hexadiene was 99.4%; the only other product of the reaction was 2,4- hexadiene. The observed first order rate constant for the reaction was 0.073 $min^{-1}$. (Rate constant)/(mmole Co)=1.83.

Comparative Example 12

The reaction was carried out in a similar manner as in Example 1. Cobalt(II) acetylacetonate (10 mg, 0.04 mmole) and dppe (32 mg, 0.08 mmole) were dissolved in 80 mL anhydrous toluene. To this was added with stirring a 25 wt % solution of diethylaluminum chloride in toluene (0.6 mL, 1.0 mmole). Butadiene (20.6 g) was added to the autoclave at 60° C., and the reaction was allowed to proceed for 60 minutes. Conversion of butadiene was 99%. Selectivity to cis-1,4-hexadiene was 99.6%; the only other product of the reaction was 2,4-hexadiene. The observed first-order rate constant for the reaction was 0.116 $min^{-1}$. (Rate constant)/(mmole Co)=2.90.

Comparative Examples 13 and 14 which follow show that a substantially slower rate of reaction results when dppe is combined with $Co(acac)_3$ and DEAC at a temperature less than 70° C. This is the case with a dppe:Co molar ratio of either 1:1 or 2:1.

Comparative Example 13

The reaction was carried out in a similar manner as in Example 1. Cobalt(III) acetylacetonate (14 mg, 0.04 mmole) and dppe (16 mg, 0.04 mmole) were dissolved in 80 mL anhydrous toluene. To this was added with stirring a 25 wt % solution of DEAC in toluene (0.6 mL, 1.0 mmole). Butadiene (20.1 g) was added to the autoclave at 60° C., and the reaction was allowed to proceed for 60 minutes. Conversion of butadiene was 99%. Selectivity to cis-1,4-hexadiene was 99.6%; the only other product of the reaction was 2,4-hexadiene. The observed first order rate constant for the reaction was 0.114 $min^{-1}$. (Rate constant)/(mmole Co)=2.85.

Comparative Example 14

The reaction was carried out in a similar manner as in Example 1. Cobalt(III) acetylacetonate (14 mg, 0.04 mmole) and dppe (32 mg, 0.08 mmole) were dissolved in 80 mL anhydrous toluene. To this was added with stirring a 25 wt % solution of DEAC in toluene (0.6 mL, 1.0 mmole). Butadiene (23.6 g) was added to the autoclave at 60° C., and the reaction was allowed to proceed for 49 minutes. Conversion of butadiene was 76%. Selectivity to cis-1,4-hexadiene was 99.7%; the only other product of the reaction was 2,4-hexadiene. The observed first order rate constant for the reaction was 0.020 $min^{-1}$. (Rate constant)/(mmole Co)=0.50.

Tables 6 and 7. The data of Examples 11, 12, 13 and 14, all obtained at a reaction temperature less than 70° C., are set forth in Table 6, in descending order of rate of reaction. The following Table 7 sets forth tabulations of data calculated from the '194 patent examples obtained at a reaction temperature less than 70° C. The quantities of $Co(acac)_n$ employed in Examples 11 through 14 are the same as the quantities employed in Example 6 for $Co(acac)_3$-dppp (toluene solvent) and Example 8 for $Co(acac)_2$-dppp (1,4-hexadiene solvent). As seen from Table 6, a catalyst system employing the ligand 1,2-bis(diphenylphosphino)ethane, or "dppe" as abbreviated herein, in combination with $Co(acac)_2$ or $Co(acac)_3$, even in the presence of a dialkylaluminum halide, and even at the same temperatures as used in Examples 6 and 8, is less than half as catalytically active as Examples 6 and 8. The reaction rates for the comparable '194 patent examples shown in Table 7 show an extremely slow reaction rate, more than 30 times slower than the rates of Examples 11 through 14. In Table 7, "EASC" is ethylaluminum sesquachloride.

TABLE 6

$Co(acac)_n$ - dppe Catalyst, DEAC Cocatalyst, Less Than 70° C.

| Ex. | Co Cmpd | Co (mmol) | Organo Aluminum Cmpd | Al (mmol) | Al/Co | Solvent | BD (gms) | BD (mol) | Di/Co | C= |
|---|---|---|---|---|---|---|---|---|---|---|
| 11 | Co(acac)2 + dppe | 0.04 | DEAC | 1.00 | 25 | toluene | 22.3 | 413 | 10,324 | C2 |
| 14 | Co(acac)3 + 2 dppe | 0.04 | DEAC | 1.00 | 25 | toluene | 23.6 | 437 | 10,926 | C2 |
| 12 | Co(acac)2 + 2 dppe | 0.04 | DEAC | 1.00 | 25 | toluene | 20.6 | 381 | 9,537 | C2 |
| 13 | Co(acac)3 + dppe | 0.04 | DEAC | 1.00 | 25 | toluene | 20.1 | 372 | 9,306 | C2 |

| Ex. | Time (min) | Temp (C.) | 1,4-HD Yield (g) | 1,4-HD Yield (mols) | Prodt'y (mol/mol) | Rate (mol/mol/min) | Observed 1st Order Rate K (min-1) | Rate/mol | Conv (%) | Select'y (%) |
|---|---|---|---|---|---|---|---|---|---|---|
| 11 | 60 | 60 | 33.32 | 0.41 | 10,142 | 169 | 0.073 | 1.83 | 99 | 99.4 |
| 14 | 49 | 60 | 27.15 | 0.33 | 8,265 | 169 | 0.02 | 0.50 | 76 | 99.7 |
| 12 | 60 | 60 | 30.84 | 0.38 | 9,388 | 156 | 0.116 | 2.90 | 99 | 99.6 |
| 13 | 60 | 60 | 30.10 | 0.37 | 9,160 | 153 | 0.114 | 2.85 | 99 | 99.6 |

TABLE 7

U.S. Pat. No. 3,405,194: $Co(acac)_3$ - dppe Catalyst, Organoaluminum Cocatalyst, Less Than 70° C.

| Ex. | Co Cmpd | Co (mmol) | Organo Aluminum Cmpd | Al (mmol) | Al/Co | Solvent | BD (gms) | BD (mol) | Di/Co |
|---|---|---|---|---|---|---|---|---|---|
| 39 | Co(acac)3 + 2.2 dppe | 1.00 | DEAC | 15.9 | 15.9 | ethane | 32.4 | 0.60 | 600 |
| 47 | Co(acac)3 + 2.2 dppe | 1.00 | EASC | 17.6 | 17.6 | toluene | 16.7 | 0.31 | 310 |

| Ex. | C= | Time (min) | Temp (C.) | 1,4-HD Yield (g) | 1,4-HD Yield (mols) | Prodt'y (mol/mol) | Rate (mol/mol/min) | Conv (%) | Select'y (%) |
|---|---|---|---|---|---|---|---|---|---|
| 39 | C2 | 120 | 50 | 42.50 | 0.52 | 517 | 4.31 | 91.31 | 94.60 |
| 47 | C2 | 1380 | 50 | 11.30 | 0.14 | 138 | 0.10 | 47.71 | 93.39 |

Having described our invention, the spirit and scope of it will be understood to those skilled in the relevant art, who will appreciate variants beyond those set forth by our specific embodiments. Our invention is not limited to the specific embodiments detailed herein, but extends to the full scope of the appended claims and the equivalents thereof.

We claim:

1. A process for preparing pure 1,4 dienes without the use of halogenated hydrocarbon solvents, which comprises: reacting a conjugated diolefin with an alpha-olefin in the presence of a cobalt catalyst system consisting essentially of:

1. $Co(acac)_n$ combined with dppp or $CoCl_2$(dppp), where acac is acetylacetonate, n equals the valence of cobalt, and dppp is 1,3-bis(diphenylphosphino)-propane, and
2. a dialkylaluminum chloride, present at a molar ratio of Al/Co of at least 5:1, in a non-halogenated hydrocarbon solvent reaction medium, at reaction conditions controlled in a temperature range less than 70° C. and an alpha-olefin partial pressure range from about 0.5 to about 100 atmospheres, effective to convert the conjugated diolefin to a 1,4-diene with essentially 100% selectivity.

2. The process of claim 1, in which said conjugated diolefin is butadiene, said alpha-olefin is ethylene and said 1,4-diene is 1,4-hexadiene.

3. The process of claim 2, in which said cobalt catalyst system is said $Co(acac)_n$ combined with dppp and wherein from about 0.9 to less than 2 mols of dppp are combined with the $Co(acac)_n$ in the reaction medium.

4. The process of claim 2, in which said cobalt catalyst system is said $Co(acac)_n$ combined with dppp and wherein, the mol ratio of dppp to $Co(acac)_n$ is effective to produce a rate of reaction, at the reaction temperature less than 70° C., of at least about 120 mols of 1,4-hexadiene per mol of cobalt per minute.

5. The process of claim 2, in which said cobalt catalyst system is said $Co(acac)_n$ combined with dppp and wherein, the mol ratio of dppp to $Co(acac)_n$ is effective for a catalyst productivity, at the reaction temperature less than 70° C., of at least about 1000 mols of 1,4-hexadiene per mol of cobalt.

6. The process of claim 1, in which said cobalt catalyst system is $Co(acac)_2$ combined with dppp and diethylaluminum chloride.

7. The process of claim 1, in which said cobalt catalyst system is $Co(acac)_3$ combined with dppp and diethylaluminum chloride.

8. The process of claim 6, in which the first order reaction rate constant per mmole of cobalt is at least about 15.

9. The process of claim 1, in which said cobalt catalyst system is $CoCl_2$(dppp) and diethylaluminum chloride.

10. The process of claim 9 in which the rate of the reaction exceeds 100 mols of 1,4-hexadiene produced per mol of cobalt per minute.

11. The process of claim 9, in which said cobalt catalyst system further includes triethylaluminum with no more than two molar equivalents of triethylaluminum per mol $CoCl_2$(dppp).

12. The process of claim 1, in which said non-halogenated hydrocarbon solvent is selected from one or more of toluene, xylene and a 1,4-diene which is the product of the reaction.

13. The process of claim 1 in which the temperature is at least about 50° C. and less than 70° C.

14. The process of claim 13, in which said temperature is about 60° C.

15. The process of claim 1 in which said conjugated diolefin is butadiene and said alpha-olefin is propylene.

16. The process of claim 15, in which said cobalt catalyst system and said reaction conditions are effective to produce a rate of reaction, at the reaction temperature less than 70° C., of at least about 30 mols of 2-methyl-1,4-hexadiene per mol of cobalt per minute.

17. The process of claim 1, in which said conjugated diolefin is isoprene and said alpha-olefin is ethylene and in which said cobalt catalyst system and said reaction conditions are effective to produce a rate of reaction, at the reaction temperature less than 70° C., of at least about 30 mols of a mixture of 4-methyl-1,4-hexadiene and 5-methyl-1,4-hexadiene per mol of cobalt per minute.

18. The process of claim 1 in which said conjugated diolefin is isoprene and said alpha-olefin is propylene.

19. A process for preparing 1,4-hexadiene, which comprises: reacting butadiene with ethylene in the presence of a cobalt catalyst system consisting of (a) Co(II)-(acetylacetonate)$_2$ and 1,3-bis(diphenylphosphino)propane in a mol ratio of about 1:1.5, and (b) diethylaluminum chloride, at a mol ratio of Al/Co of at least 5:1, in a non-halogenated hydrocarbon solvent at reaction conditions controlled in a temperature range from about 50° C. to 69° C. and an ethylene partial pressure range from about 0.5 to about 100 atmospheres, effective to convert the butadiene to a 1,4-hexadiene with essentially 100% selectivity at a reaction rate of at least 500 mols of 1,4-hexadiene produced per mol of cobalt per minute.

* * * * *